(12) United States Patent
Tsuchino

(10) Patent No.: US 6,431,440 B1
(45) Date of Patent: *Aug. 13, 2002

(54) RADIATION IMAGE READING METHOD AND RADIATION IMAGE READING APPARATUS

(75) Inventor: Hisanori Tsuchino, Hino (JP)

(73) Assignee: Konica Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/264,842

(22) Filed: Mar. 8, 1999

(51) Int. Cl.⁷ .................................................. G06K 5/00

(52) U.S. Cl. .................................. 235/380; 235/462.13

(58) Field of Search ................................. 235/375, 380, 235/383, 385, 462.13, 486, 487; 705/2, 3; 378/165; 250/580

(56) References Cited

U.S. PATENT DOCUMENTS

| | | | | |
|---|---|---|---|---|
| 4,855,468 A | * | 8/1989 | Shimura | 250/327.2 |
| 4,896,027 A | * | 1/1990 | Drexler | 235/487 |
| 5,418,355 A | * | 5/1995 | Weil | 235/375 |
| 5,592,374 A | * | 1/1997 | Fellegara et al. | 235/375 |
| 5,865,745 A | * | 2/1999 | Schmitt et al. | 250/580 |

* cited by examiner

*Primary Examiner*—Karl D. Frech
(74) *Attorney, Agent, or Firm*—Frishauf, Holtz, Goodman & Chick, P.C.

(57) ABSTRACT

There is described a method and an apparatus for reading a radiation image recorded on a radiation image conversion panel. The apparatus includes a receiving device for receiving a plurality of patient information incoming from outside, an inputting device for inputting patient identification information, a comparing device for comparing the patient information with the patient identification information, a reading device for reading the radiation image conversion panel to generate a radiation image, and a controller for correlating the patient information with the radiation image generated by the reading device.

15 Claims, 4 Drawing Sheets

RADIATION IMAGE READING METHOD AND RADIATION IMAGE READING APPARATUS

BACKGROUND OF THE INVENTION

The present invention relates to a radiation image reading method and a radiation image reading apparatus in both of which a radiation image recording panel, which utilizes, for example, a semiconductor detector, a stored phosphor (a stimulative phosphor plate), etc., is employed.

When a certain kind of phosphor is irradiated by radiations (X-rays, alpha rays, beta rays, gamma rays or ultraviolet rays), a part of radiation energy is stored in the phosphor. Then, when the phosphor is irradiated by excitation light such as visible light, the phosphor shows its stimulated emission according to the stored energy, which has so far been known. A phosphor showing this characteristic is called a stored phosphor or a stimulative phosphor.

It is possible that radiation image information of the human body is temporarily recorded on a stored phosphor (stimulative phosphor plate) provided on a sheet, by means of the stimulative phosphor, then, the stimulative phosphor plate is scanned by excitation light such as a laser beam to generate stimulated emission light, and the stimulated emission light thus obtained is read photoelectrically to obtain image signals.

Recently, another technique has been set forth in Tokkaihei 9-90048, which describes a method of generating a radiation image information by irradiating radial rays penetrated through a subject onto the semiconductor detector.

In a hospital, patients from a plurality of diagnosis & treatment departments are radiographed in a radiographic inspection room to obtain radiation images. Therefore, correlation between a patient and a radiographed image (or between a patient and a radiation image conversion panel) is sometimes difficult.

SUMMARY OF THE INVENTION

When the correlation between a patient and a radiographed image is not correct, a diagnosis is made undesirably by the use of wrong radiation image information, resulting in a possibility that improper medical treatment is given to the patient.

The invention has been achieved to solve the problems stated above, and an object of the invention is to materialize a radiation image reading method and a radiation image reading apparatus in both of which a radiation image and a patient representing an object can be correlated accurately.

Accordingly, to overcome the abovementioned problems, a method and an apparatus for reading a radiation image, embodied in the present invention, will be described as follows:

(1). The method of reading a radiation image, comprising steps of:

receiving a plurality of patient information;

inputting patient identification information;

comparing the patient information with the patient identification information to confirm an agreement between them;

reading a radiation image information recorded on a radiation image conversion panel; and correlating the patient information with the radiation image information.

(2). The radiation image reading apparatus for reading a radiation image conversion panel, comprising:

receiving means for receiving a plurality of patient information incoming from outside;

inputting means for inputting patient identification information when reading the radiation image conversion panel or when radiographing a patient;

comparing means for comparing the patient information with the patient identification information to confirm an agreement between them;

reading means for reading the radiation image conversion panel to generate a radiation image; and control means for correlating the patient information with the radiation image generated by the reading means.

In the abovementioned method and apparatus, it is not necessarily required in the comparing step that the patient information just coincides with the patient identification information as the same data, but it is acceptable to merely confirm that a patient designated by the patient information is the same person as a patient designated by the patient identification information.

Further, to overcome the abovementioned problems, other methods and apparatus, embodied in the present invention, will be described as follows:

(1) A radiation image reading method for reading a radiation image conversion panel, wherein information of plural patients are received from the outside, patient identification information is inputted when a radiation image is read, then, agreement between the patient information and the patient identification information is confirmed, and the radiographed radiation image conversion panel is read to generate a radiation image which is correlated with the aforementioned patient information.

In the radiation image reading method mentioned above, patient identification information which identifies a patient is inputted when a radiation image is read, and pieces of information of plural patients received from the outside through a network are checked in terms of agreement with the inputted patient identification information, thus, the patient information confirmed in terms of agreement is correlated with the radiation image.

By correlating the patient information with a radiation image by using the patient identification information as stated above, the radiation image can be correlated accurately with a patient representing an object.

(2) A radiation image reading method for reading a radiation image conversion panel, wherein information of plural patients are received from the outside, patient identification information is inputted when a radiation image is radiographed, then, agreement between the patient information and the patient identification information is confirmed, and the radiographed radiation image conversion panel is read to generate a radiation image which is correlated with the aforementioned patient information.

In the radiation image reading method mentioned above, patient identification information which identifies a patient is inputted in the course of radiographing a radiation image, and pieces of information of plural patients received from the outside through a network are checked in terms of agreement with the inputted patient identification information, thus, the patient information confirmed in terms of agreement is correlated with the radiation image.

By correlating the patient information with a radiation image by using the patient identification information as stated above, the radiation image can be correlated accurately with a patient representing an object.

(3) The radiation image reading method of (1) or (2) above, wherein input of the patient identification information is conducted by reading a magnetic card.

In the radiation image reading method stated above, reading of a magnetic card makes patient identification information to be inputted. It is therefore possible to identify a patient quickly and surely by making the magnetic card brought in by the patient to be read.

By using this patient identification information, patient information can be correlated with a radiation image accurately, and thereby, the radiation image can accurately be correlated with a patient representing an object.

(4) The radiation image reading method of (2) or (3) above, wherein input of the patient identification information is conducted through inputting operations of confirmation after display of patient information received from the outside.

In this radiation image reading method, operations of confirmation make patient identification information to be inputted. It is therefore possible to identify a patient quickly and surely.

By using this patient identification information. patient information can be correlated with a radiation image accurately, and thereby, the radiation image can accurately be correlated with a patient which is an object.

(5) A radiation image reading apparatus for reading a radiation image conversion panel, wherein a patient information receiving means which receives information of plural patients from the outside, an inputting means where input of patient identification information is conducted in the case of reading or radiographing of a radiation image, an agreement-confirming means which confirms agreement between the aforementioned patient information and patient identification information, a reading means which reads the radiographed radiation image conversion panel and generates a radiation image, and a control means which correlates the radiation image generated by the reading means with the aforesaid patient information, are provided.

In this radiation image reading apparatus, patient identification information which identifies a patient is inputted from the inputting means in the case of radiographing of a radiation image, then, pieces of information of plural patients received from the outside through a network are checked by the agreement-confirming means in terms of agreement with the inputted patient identification information, thus, the patient information confirmed in terms of agreement is correlated with the radiation image by the control means.

Incidentally, the agreement-confirming means and the control means can be materialized by a CPU or true action program of the radiation image reading apparatus.

As stated above, by correlating patient information with a radiation image by using patient identification information from the inputting means, it is possible to correlate the radiation image with a patient representing an object accurately.

(6) The radiation image reading apparatus according to (5) above, wherein the inputting means is equipped with a magnetic card reader, and the agreement-confirming means confirms agreement between the patient information and the patient identification information by the use of results of reading conducted by the magnetic card reader.

In this radiation image reading apparatus, reading of a magnetic card conducted by the inputting means makes patient identification information to be inputted. It is therefore possible to identify a patient quickly and surely by reading the magnetic card which has been brought in by the patient.

As stated above, by correlating patient information with a radiation image by using patient identification information from the inputting means, it is possible to correlate the radiation image with a patient representing an object accurately.

(7) The radiation image reading apparatus according to (5) above, wherein a display means which displays patient information received from the outside is provided, and the patient identification information is inputted based on inputting operations of confirmation conducted by the inputting means after display of patient information on the display means.

In this radiation image reading apparatus, it is possible to identify a patient quickly and surely, because patient identification information is inputted through operations of confirmation conducted by the inputting means.

As stated above, by using patient identification information from the inputting means, it is possible to correlate patient information with a radiation image accurately, and thereby to correlate the radiation image with a patient representing an object accurately.

(8) The radiation image reading apparatus according to (5)–(7) above, wherein a panel discrimination information reading means which reads discrimination information of a radiation image conversion panel is provided, and the control means mentioned above correlates the radiation image with the patient information by correlating the patient information confirmed in terms of agreement by the agreement-confirming means with discrimination information of the radiation image conversion panel.

In this radiation image reading apparatus, patient information confirmed in terms of agreement is correlated with a plate, and the radiation image information read from the plate is correlated with patient information.

As stated above, by correlating patient information with a radiation image by using discrimination information of the plate, it is possible to correlate radiation image with a patient representing an object accurately.

BRIEF DESCRIPTION OF THE DRAWINGS

Other objectives and advantages of the present invention will become apparent upon reading the following detailed description and upon reference to the drawings in which.

DETAILED DESCRIPTION OF THE PREFERRED EMBODIMENT

Next, an embodiment of the invention will be explained as follows, referring to drawings.

Figure 1:
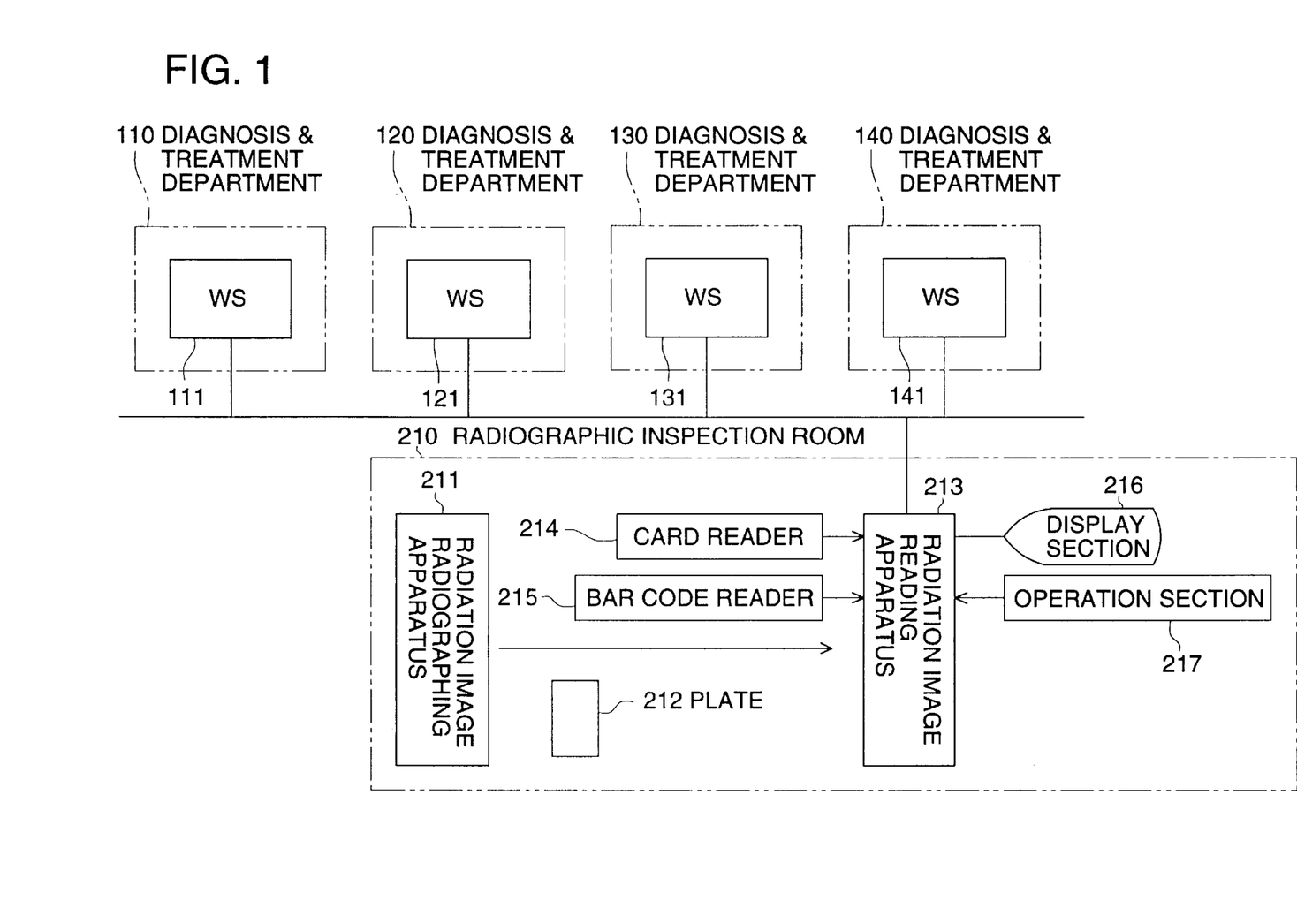
FIG. 1 is a structure diagram showing the structure of a radiation image reading apparatus used in an embodiment of the invention and its surroundings.

FIG. 1 represents a block diagram including constitution of each section in the surrounding of a radiation image reading apparatus used in each embodiment of the invention, and it also represents an example of an apparatus with which a radiation image reading method in each embodiment of the invention is put into practice. Further, the constitution in FIG. 1 is illustratively shown in FIG. 3 as a perspective view.

In FIG. 1, each of 110, 120, 130 and 140 represents a diagnosis & treatment department where each of terminals (hereinafter referred to as WS) 111, 121, 131 and 141 connected to the network is provided for inputting patient information.

Incidentally, as used herein, the term patient information mentioned above is defined as information pertaining to a patient, e-g., including name, age, sex, a part of patient's body to be radiographed, etc. In the present embodiment, the patient information is transmitted from each of diagnosis & treatment departments and is received by a receiving means of the radiation image reading apparatus installed in a radiographic inspection room.

The numeral 210 represents a radiographic inspection room where radiographing and reading of a radiation image are conducted, and radiation image radiographing apparatus 211 which radiographs using plate 212 representing a medium for radiographing such as a radiation image conversion panel and radiation image reading apparatus 213 which reads radiographed plate 212 are provided in the radiographic inspection room.

The radiation image reading apparatus 213 is connected to WS 111–141 through the network, and it is also connected to card reader 214 serving as an inputting means which inputs patient identification information in the case of radiographing of a radiation image, bar-code reader 215 serving as a panel discrimination information reading means which reads discrimination information of the plate 212, display section 216 serving as a display means having therein a CRT monitor or the like displaying patient information received from the outside through the network, and operation section 217 serving as an inputting means which inputs confirmation of patient identification information after the patient information is displayed on the display section 216.

As the inputting means, in this case, it is possible to use various means which can identify patients (inputting of patient identification information) which are exemplified by the following;

a card reader which reads a magnetic card brought in by a patient, an operation section with which registered patient information is displayed on a monitor screen, a patient is called by an operator based on the display, and the operator presses down a confirmation key at a point of time when a response of the patient is confirmed, and an operation section with which a voice composing unit calls a patient for registered patient information based on the order of registration, and the patient presses down a confirmation key.

Though a bar-code reader is shown here as an example of a panel discrimination information reading means, various means capable of recognizing panel discrimination information such as an IC card reader and a magnetic tape reader are to be included as other items.

Figure 3:
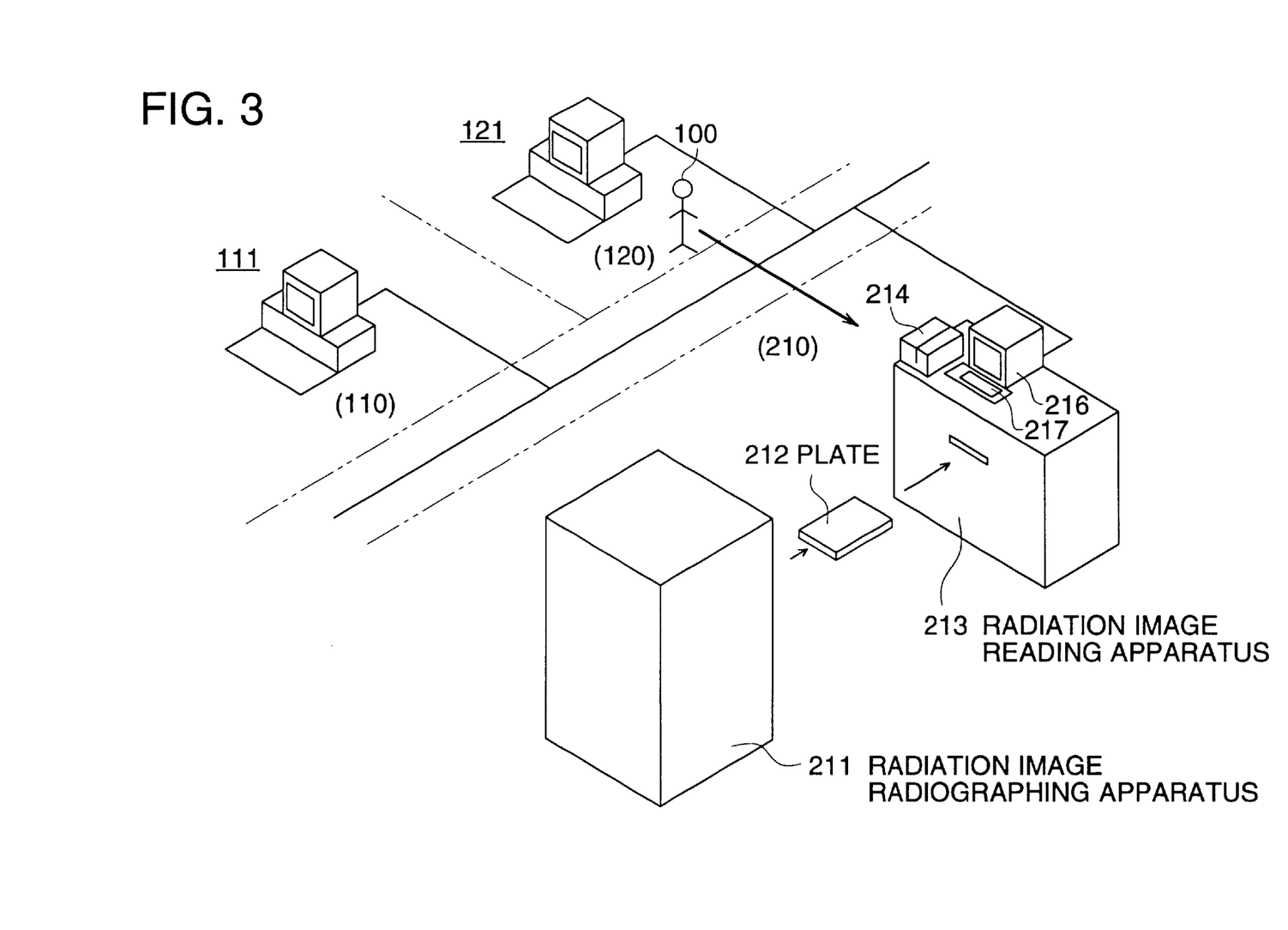
FIG. 3 is an illustration showing the structure of a radiation image reading apparatus used in an embodiment of the invention and its surroundings.

Incidentally, FIG. 3 illustratively shows how a patient 100 moves from diagnosis & treatment department 120 to the radiographic inspection room 210.

<First Embodiment>

Now, operations in the first embodiment will be explained with reference to the flow chart shown in FIG. 2. The flow chart in FIG. 2 is a routine of control in reading radiation images of plural patients.

First of all, a patient takes various medical advice from a doctor and receives directions in each diagnosis & treatment department. Here, an occasion wherein a patient receives directions for radiation image radiographing in each diagnosis & treatment department will be explained. In this case, various types of information of the patient (patient information) are inputted in each diagnosis & treatment department (FIG. 2 S1), and this patient information is transferred to radiation image reading apparatus 213 of radiographic inspection room 210 through a network. In the example shown in FIG. 3, patient information from diagnosis & treatment department 120 is transferred to radiation image reading apparatus 213 through the network.

Incidentally, when patient information has already been inputted at a terminal such as a reception office, data of radiographing for radiation images are added to the patient information which is then transferred from each diagnosis & treatment department to radiation image reading apparatus 213 of radiographic inspection room 210 through the network.

Figure 2:
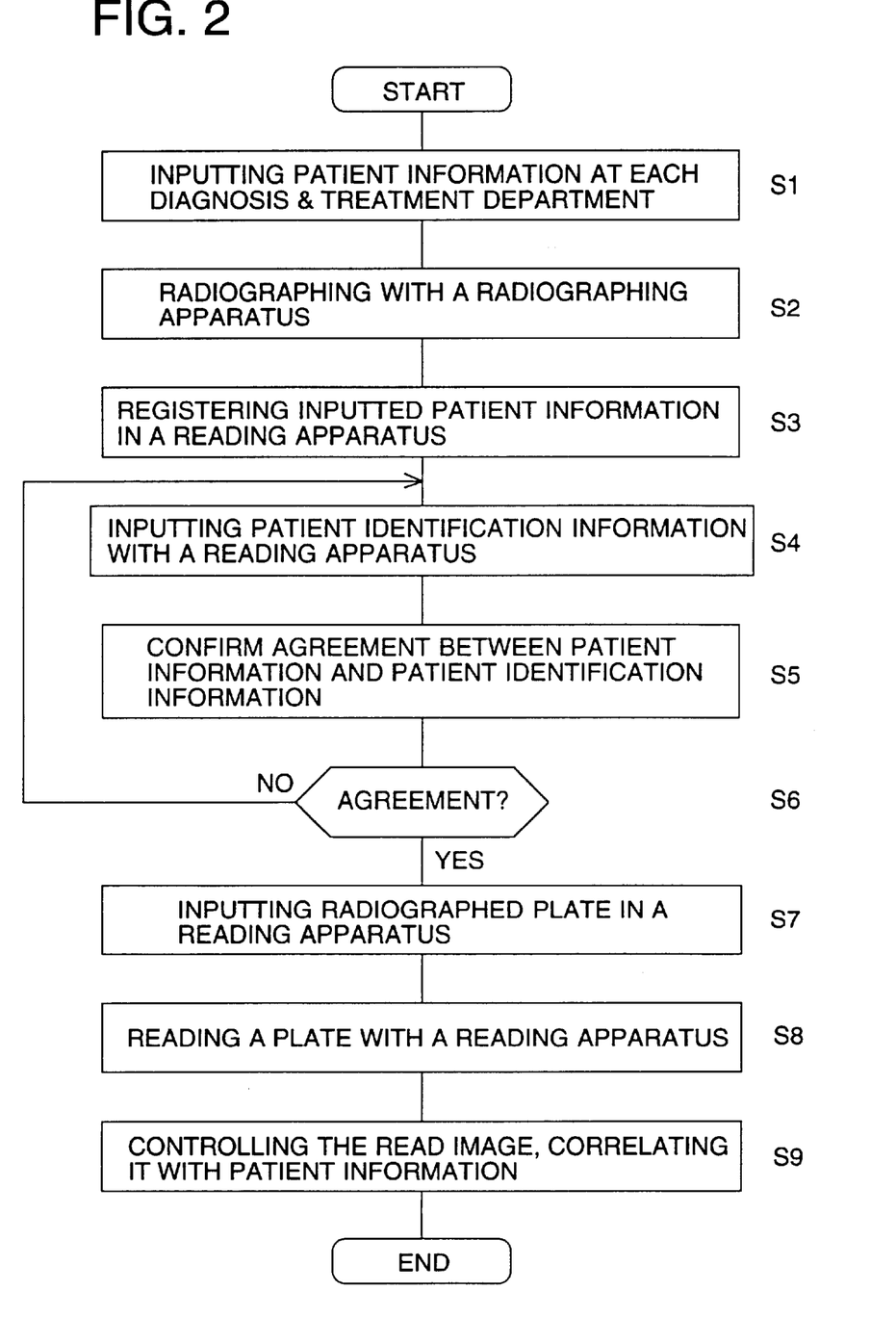
FIG. 2 is a flow chart showing how a radiation image reading apparatus of the first embodiment of the invention reads.

Now, in the radiographic inspection room 210, a patient is radiographed by radiation image radiographing apparatus 211 to obtain a radiation image (FIG. 2 S2).

Then, patient information sent from each diagnosis & treatment department is received by radiation image reading apparatus 213, and then is registered (FIG. 2 S3). Since patient information is sent from each diagnosis & treatment department as stated, the radiation image reading apparatus 213 is to be provided with functions to receive and register information of plural patients. Therefore, the radiation image reading apparatus 213 is provided therein with a receiving means which receives patient information through a network and a control means which registers patient information.

Incidentally, the aforementioned radiographing (FIG. 2 S2) and registration of patient information (FIG. 2 S3) may either be conducted in this order or may be conducted in the opposite order, or they may be conducted simultaneously, representing that the sequence of them does not matter.

In the course of reading, an operator conducts patient identification and inputs patient identification information (FIG. 2 S4).

The following method is taken for the patient identification (input of patient identification information).

A magnetic card brought in by a patient is read by card reader 214.

Owing to the input of patient identification information, a patient corresponding to the radiation image data radiographed on plate 212 can be identified on the radiation image reading apparatus 213.

In this case, the radiation image reading apparatus 213 confirms agreement between the registered information of plural patients and the inputted patient identification information (FIG. 2 S5). Incidentally, this confirmation of agreement is conducted by a CPU constituting a means to confirm agreement in the radiation image reading apparatus 213.

For example, when a magnetic card brought in by a patient is read with input of the aforesaid patient identification information, agreement between patient's ID and name obtained from the magnetic card and patient information sent from each diagnosis & treatment department is confirmed, and agreed patient information is extracted (FIG. 2 S6).

At the point of time when the confirmation of agreement mentioned above is completed, plate 212 is inserted in the radiation image reading apparatus 213 (FIG. 2 S7). Then, the radiation image reading apparatus 213 reads the inserted plate 212 (FIG. 2 S8).

On the radiation image reading apparatus 213, a radiation image radiographed on the plate 212 is read, and radiation image data are generated.

Then, patient information is correlated with the radiation image data generated through reading (FIG. 2 S9). After that, the radiation image data and the patient information thus correlated are stored in a prescribed storage device. Incidentally, such correlating and data storing are conducted by a control means (such as the above-mentioned CPU or the like) in the radiation image reading apparatus 213.

By correlating patient information with a radiation image by the use of patient identification information as stated above, it is possible to conduct correlating accurately between the radiation image and a patient representing an object.

By correlating patient information which has been confirmed in terms of agreement with discrimination information of plate 212 temporarily, and thereby, by correlating radiation image information obtained by reading the plate 212 with the patient information, it is possible to conduct accurate correlating between a radiation image and a patient representing an object, in spite of an environment in which plural plates are present and the order of radiographing and reading varies. Therefore, correspondence between a radiation image and a patient is not disturbed even when the order of radiographing and reading is interrupted.

<Second embodiment>

Figure 4:
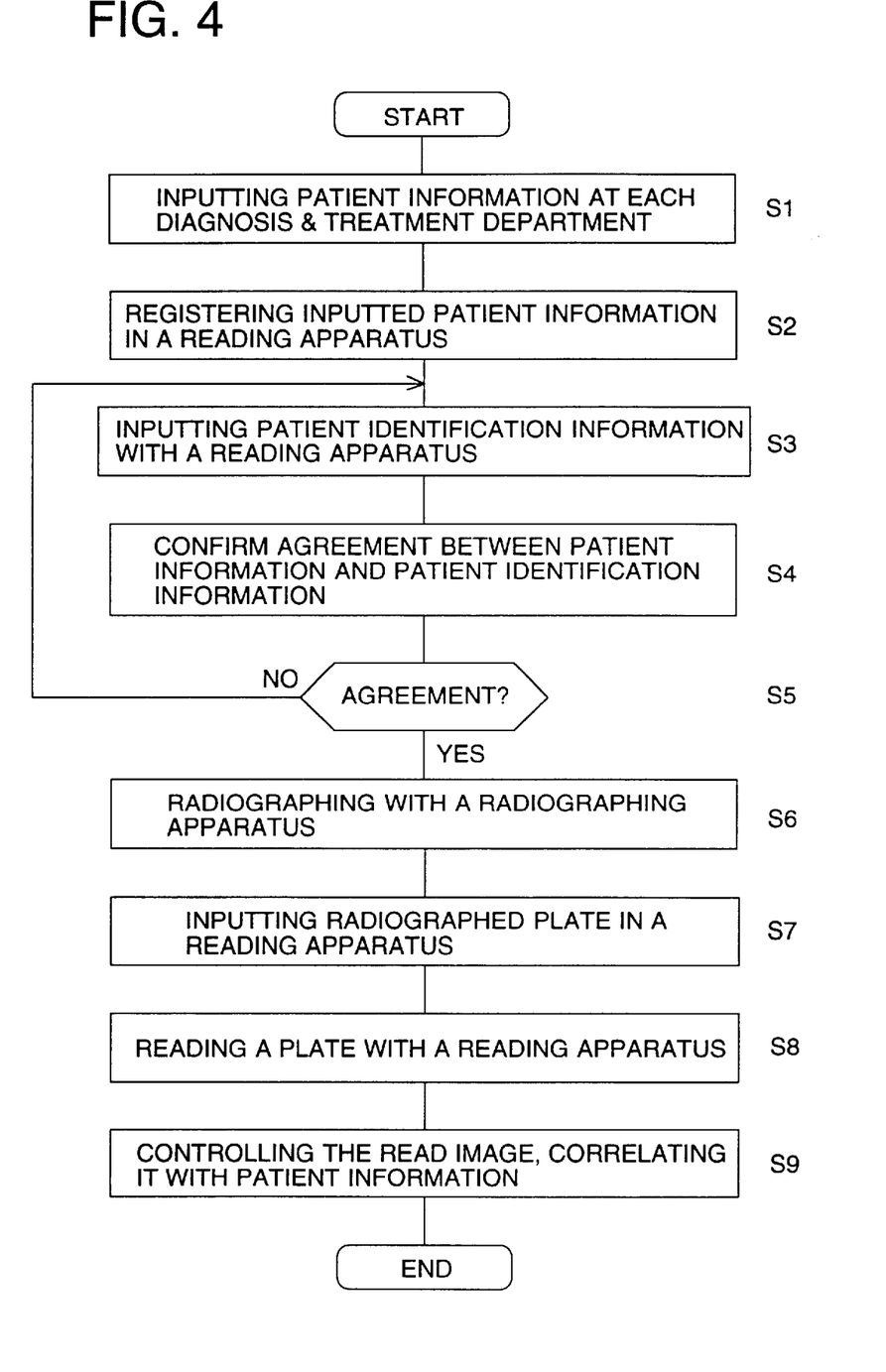
FIG. 4 is a flow chart showing how a radiation image reading apparatus of the second embodiment of the invention reads.

Now, operations in the second embodiment will be explained with reference to the flow chart shown in FIG. 4. The flow chart in FIG. 4 is a routine of control in reading radiation images of plural patients.

First of all, a patient takes various medical advice from a doctor and receives directions in each diagnosis & treatment department. Here, an occasion wherein a patient receives directions for radiation image radiographing in each diagnosis & treatment department will be explained. In this case, various types of information of the patient (patient information) are inputted in each diagnosis & treatment department (FIG. 4 S1), and this patient information is transferred to radiation image reading apparatus 213 of radiographic inspection room 210 through a network. In the example shown in FIG. 3, patient information from diagnosis & treatment department 120 is transferred to radiation image reading apparatus 213 through the network.

Incidentally, when patient information has already been inputted at a terminal such as a reception office, data of radiographing for radiation images are added to the patient information which is then transferred from each diagnosis & treatment department to radiation image reading apparatus 213 of radiographic inspection room 210 through the network.

Patient information sent from each diagnosis & treatment department in the aforesaid manner is received by radiation image reading apparatus 213, and then is registered (FIG. 4 S2) for preparation of radiographing of radiation images. Incidentally, since patient information is sent from each diagnosis & treatment department, the radiation image reading apparatus 213 is to be provided with functions to receive and register information of plural patients. Therefore, the radiation image reading apparatus 213 is provided therein with a receiving means which receives patient information through a network and a control means which registers patient information.

When a patient from each diagnosis & treatment department enters radiographic inspection room 210, an operator in the radiographic inspection room 210 inputs patient identification information after confirming the patient. The following methods are taken for the patient identification (input of patient identification information).

(1) A magnetic card brought in by a patient is read by card reader 214.

(2) Registered patient information is displayed on display section 216, then, an operator calls a patient based on the display, and the operator presses down a confirmation key from operation section 217 at the moment when the response of the patient is confirmed.

(3) A voice composing unit calls a patient for registered patient information based on the order of registration, and the patient presses down a confirmation key from operation section 217.

Owing to this input of patient identification information, a patient who is waiting for radiographing in radiographic inspection room 210 (a patient to be radiographed) can be identified.

In this case, the radiation image reading apparatus 213 confirms agreement between the registered information of plural patients and the inputted patient identification information (FIG. 4 S4). Incidentally, this confirmation of agreement is conducted by a CPU constituting a means to confirm agreement in the radiation image reading apparatus 213.

For example, when a magnetic card brought in by a patient is read with input (1) of the aforesaid patient identification information, agreement between patient's ID and name obtained from the magnetic card and patient information sent from each diagnosis & treatment department is confirmed, and agreed patient information is extracted (FIG. 4 S5). Incidentally, in the case of input (2) of the aforesaid patient identification information, input of the patient identification information and confirmation of agreement have been finished by the operator. Therefore, the confirmation of agreement is not necessary in this stage.

Further, a bar-code (discrimination information of a plate) given to plate 212 which is used for radiographing is read by bar-code reader 215, simultaneously with operations of the confirmation of agreement stated above. Data of the bar-code thus read are correlated with the patient information extracted by the aforesaid confirmation of agreement.

Then, radiographing for a radiation image of a patient is carried out by radiation image radiographing apparatus 211 (FIG. 4 S6). At the moment of completion of radiographing, the plate 212 is taken out of the radiation image radiographing apparatus 211, and is inserted in radiation image reading apparatus 213 (FIG. 4 S7). Then, the inserted plate 212 is read by the radiation image reading apparatus 213 (FIG. 4 S8).

On the radiation image reading apparatus 213, a bar-code on the plate 212 and a radiation image formed on the plate 212 through radiographing are read by bar-code reader 215 or by a built-in bar-code reader, and radiation image data are generated.

Referring to the bar-code on the plate 212 read by the bar-code reader, patient information correlated on the bar-code is correlated with the radiation image data generated through the reading (FIG. 4 S9). Then, the radiation image data and the patient information thus correlated are stored in a prescribed storage device. Incidentally, such correlating and data storing are conducted by a control means (such as the above-mentioned CPU or the like) in the radiation image reading apparatus 213.

By correlating patient information with a radiation image by the use of patient identification information as stated above, it is possible to conduct correlating accurately between the radiation image and a patient representing an object.

By correlating patient information which has been confirmed in terms of agreement with discrimination information of plate 212 temporarily, and thereby, by correlating radiation image information obtained by reading the plate 212 with the patient information, it is possible to conduct accurate correlating between a radiation image and a patient representing an object, in spite of an environment in which plural plates are present and the order of radiographing and reading varies. Therefore, correspondence between a radiation image and a patient is not disturbed even when the order of radiographing and reading is interrupted.

<Other embodiments>

(1) Though a magnetic card is used for inputting patient identification information in each example of the embodiment stated above, it is also possible to use various other methods.

(2) When a rewritable magnetic tape is attached to plate 212 in place of an exclusive bar-code, it is also possible to correlate radiation image data with patient information when reading a radiation image on the radiographed plate 212, by storing patient information temporarily on the plate 212 side when reading data on the plate 212 before radiographing.

(3) Though only one radiographic inspection room 210 is indicated in the structure shown in FIG. 1, plural radiographic inspection rooms. 210 can sometimes be present. In that case, a server which assigns data from each diagnosis & treatment department to corresponding a radiographic inspection room can be provided.

(4) Though a radiation image radiographing apparatus and a radiation image reading apparatus are shown to be separate from each other in each of FIGS. 1 and 3, both the first embodiment and the second embodiment can be applied to a radiation image radiographing/reading apparatus (built-in type) capable of radiographing and reading. In that case, reading of a bar-code on the plate in the above explanation is not necessary.

As explained in detail above, each invention described hereupon can offer the following effects.

(1) In the invention, patient identification information identifying a patient is inputted when reading a radiation image, then, confirmation of agreement between information of plural patients received from the outside through a network and the inputted patient identification information is conducted, and the patient information confirmed to agree with the inputted patient identification information is correlated with a radiation image.

By correlating patient information with a radiation image by the use of patient identification information as stated above, it is possible to correlate the radiation image with a patient representing an object accurately.

(2) In the invention, in the case of radiographing for a radiation image, patient identification information which identifies a patient is inputted, then, confirmation of agreement between information of plural patients received from the outside through a network and the inputted patient identification information is conducted, and the patient information confirmed to agree with the inputted patient identification information is correlated with a radiation image.

By correlating patient information with a radiation image by the use of patient identification information as stated above, it is possible to correlate the radiation image with a patient representing an object accurately.

(3) Since patient identification information is inputted when a magnetic card is read in the invention, it is possible to identify the patient quickly and surely by making the magnetic card brought by the patient to be read.

Using such patient identification information as those stated above makes it possible to correlate patient information with a radiation image accurately, and to accurately correlate the radiation image with a patient representing an object.

(4) Since patient identification information is inputted by operation of identification in the invention, it is possible to identify the patient quickly and surely.

Using such patient identification information as those stated above makes it possible to correlate patient information with a radiation image accurately, and to accurately correlate the radiation image with a patient representing an object.

(5) In the invention, when reading a radiation image or radiographing for a radiation image, patient identification information which identifies a patient is inputted from an input means, then an agreement-confirming means confirms agreement between information of plural patients received from the outside through a network and the inputted patient identification information, and a control means correlates the agreement-confirmed patient information with a radiation image.

By correlating the patient information and a radiation image by the use of patient identification information coming from an input means as stated above, it is possible to correlate a radiation image with a patient representing an object accurately.

(6) Since patient identification information is inputted when a magnetic card is read by an inputting means in the invention, it is possible to identify a patient quickly and surely by making a magnetic card brought by a patient to be read.

By correlating patient information with a radiation image by the use of patient identification information coming from an inputting means as stated above, accurate correlating between a radiation image and a patient representing an object can be carried out.

(7) Since patient identification information is inputted by operation of identification conducted by an inputting means in the invention, it is possible to identify a patient quickly and surely.

As stated above, using of patient identification information coming from an inputting means makes it possible to correlate patient information with a radiation image accurately, and to correlate the radiation image with a patient representing an object accurately.

(8) In the invention, patient information confirmed in terms of agreement is correlated with a plate in advance, and radiation image information read from the plate is correlated with patient information. Therefore, it is possible to conduct accurate correlating between a radiation image and a patient representing an object, in spite of an environment in which plural plates are present and the order of radiographing and reading is varied.

What is claimed is:

1. A radiation image recording method comprising:

registering a plurality of patient radiography data sets in a database, wherein each patient radiography data set includes patient data including patient ID data of a patient and radiography data for radiographing the patient so that the plurality of patient radiography data sets include plural different patient ID data of plural different patients;

inputting patient ID data of a given patient from a radiographing section for checking at the radiographing section before radiographing the given patient whether or not the same patient ID data as the inputted patient ID data of the given patient is registered in the database among the plural different patient ID data of the plurality of patient radiography data sets in the database;

retrieving a corresponding patient radiography data set including the same patient ID data from the database at the radiographing section when the same patient ID data as the inputted patient ID data of the given patient is registered in the database; and thereafter radiographing the given patient at the radiographing section based on radiography data included in the retrieved patient radiography data set so that a radiation image of the given patient is recorded on a recording panel.

2. The method of claim 1, wherein the plurality of patient radiography data sets are registered in the database at the radiographing section.

3. The method of claim 2, wherein the plurality of patient radiographing data sets registered in the database are received from a diagnosis section through a network.

4. The method of claim 2, the patient ID data of the given patient is inputted from an ID card of the given patient through a card reader.

5. The method of claim 2, wherein the ID card is a magnetic card.

6. The method of claim 2, wherein the plurality of patient radiography data sets are displayed on a display, and the patient ID data of the given patient is inputted based on the plurality of displayed patient radiography data sets.

7. The method of claim 1, further comprising reading the radiation image of the given patient recorded on the recording panel so as to produce radiation image data of the given patient, and recording the radiation image data of the given patient in correlation with the patient ID data of the given patient in a memory.

8. The method of claim 7, wherein the recording panel is provided with panel ID data and the panel ID data is correlated with the patient ID data of the given patient in the memory.

9. A radiation image recording apparatus comprising:

a registering device for registering a plurality of patient radiography data sets in a database, wherein each patient radiography data set includes patient data including patient ID data of a patient and radiography data for radiographing the patient so that the plurality of patient radiography data sets include plural different patient ID data of plural different patients;

an input device provided at a radiographing section for inputting patient ID data of a given patient for checking at the radiographing section before radiographing the given patient whether or not the same patient ID data as the inputted patient ID data of the given patient is registered in the database among the plural different patient ID data of the plurality of patient radiography data sets in the database;

a retrieval device for retrieving a corresponding patient radiography data set including the same patient ID data from the database at the radiographing section when the same patient ID data as the inputted patient ID data of the given patient is registered in the database; and a radiographing device for radiographing the given patient at the radiographing section based on radiography data included in the retrieved patient radiography data set so that a radiation image of the given patient is recorded on a recording panel.

10. The apparatus of claim 9, further comprising a communication device for receiving the patient radiography data sets from a diagnosis section through a network.

11. The apparatus of claim 9, wherein the input device comprises a card reader for reading an ID card of the given patient.

12. The apparatus of claim 11, wherein the ID card is a magnetic card.

13. The apparatus of claim 9, further comprising a display on which the plurality of patient radiography data sets are displayed, and wherein the patient ID of the given patient is inputted by the input device based on the plurality of patient radiography data sets displayed on the display.

14. The apparatus of claim 9, further comprising:

a reading device for reading the radiation image of the patient on the recording panel so as to produce radiation image data of the given patient; and a recording device for recording the radiation image data of the given patient in correlation with the patient ID data of the given patient in a memory.

15. The apparatus of claim 14, wherein the recording panel is provided with panel ID data and the patient ID data of the given patient is correlated with the panel ID data in the memory.

* * * * *

UNITED STATES PATENT AND TRADEMARK OFFICE
CERTIFICATE OF CORRECTION

PATENT NO.   : 6,431,440 B1
DATED        : August 13, 2002
INVENTOR(S)  : Hisanori Tsuchino It is certified that error appears in the above-identified patent and that said Letters Patent is hereby corrected as shown below:

<u>Title page,</u>
Insert Item -- [30]    Foreign Application Priority Data

Mar. 17, 1998    Japan    10-067108 --.

Signed and Sealed this

Tenth Day of June, 2003

JAMES E. ROGAN
*Director of the United States Patent and Trademark Office*